United States Patent [19]

Sheets et al.

[11] 4,246,794
[45] Jan. 27, 1981

[54] APPARATUS AND METHOD FOR ULTRASONIC INSPECTION OF ROUND STOCK SUCH AS TUBING, PIPE AND ROD

[75] Inventors: Harold L. Sheets, Chesapeake, Ohio; James H. Rowsey, Huntington, W. Va.

[73] Assignee: Huntington Alloys, Inc., Huntington, W. Va.

[21] Appl. No.: 59,683

[22] Filed: Jul. 23, 1979

Related U.S. Application Data

[63] Continuation of Ser. No. 909,769, May 26, 1978, abandoned.

[51] Int. Cl.³ .............................................. G01N 29/04
[52] U.S. Cl. ..................................................... 73/637
[58] Field of Search .................. 73/637, 638, 622, 640

[56] References Cited

U.S. PATENT DOCUMENTS

| 3,105,380 | 10/1963 | Stebbins | 73/637 |
| 3,272,000 | 9/1966 | Stebbins | 73/637 |

FOREIGN PATENT DOCUMENTS

540204 2/1977 U.S.S.R. ..................................... 73/637

OTHER PUBLICATIONS

TAC Technical Instruments Corp. Bulletin 440, "Model 44, 3-Probe Follower for Immersed Ultrasonic Inspection of Cyl. Material," Jan. 1974 (4 pages).

*Primary Examiner*—Anthony V. Ciarlante
*Attorney, Agent, or Firm*—Raymond J. Kenny; Ewan C. MacQueen

[57] ABSTRACT

Directed to non-destructive testing, particularly ultrasonic inspection of round stock such as tubing, pipe and rod wherein the inspection is conducted within a water tank to provide ultrasonic coupling of the ultrasonic probe or probes employed wherein the distance between the probe or probes and the surface of the round stock being inspected is maintained essentially constant during the course of the test to assure reliable inspection results and wherein the materials handling aspects of the testing are simplified.

6 Claims, 19 Drawing Figures

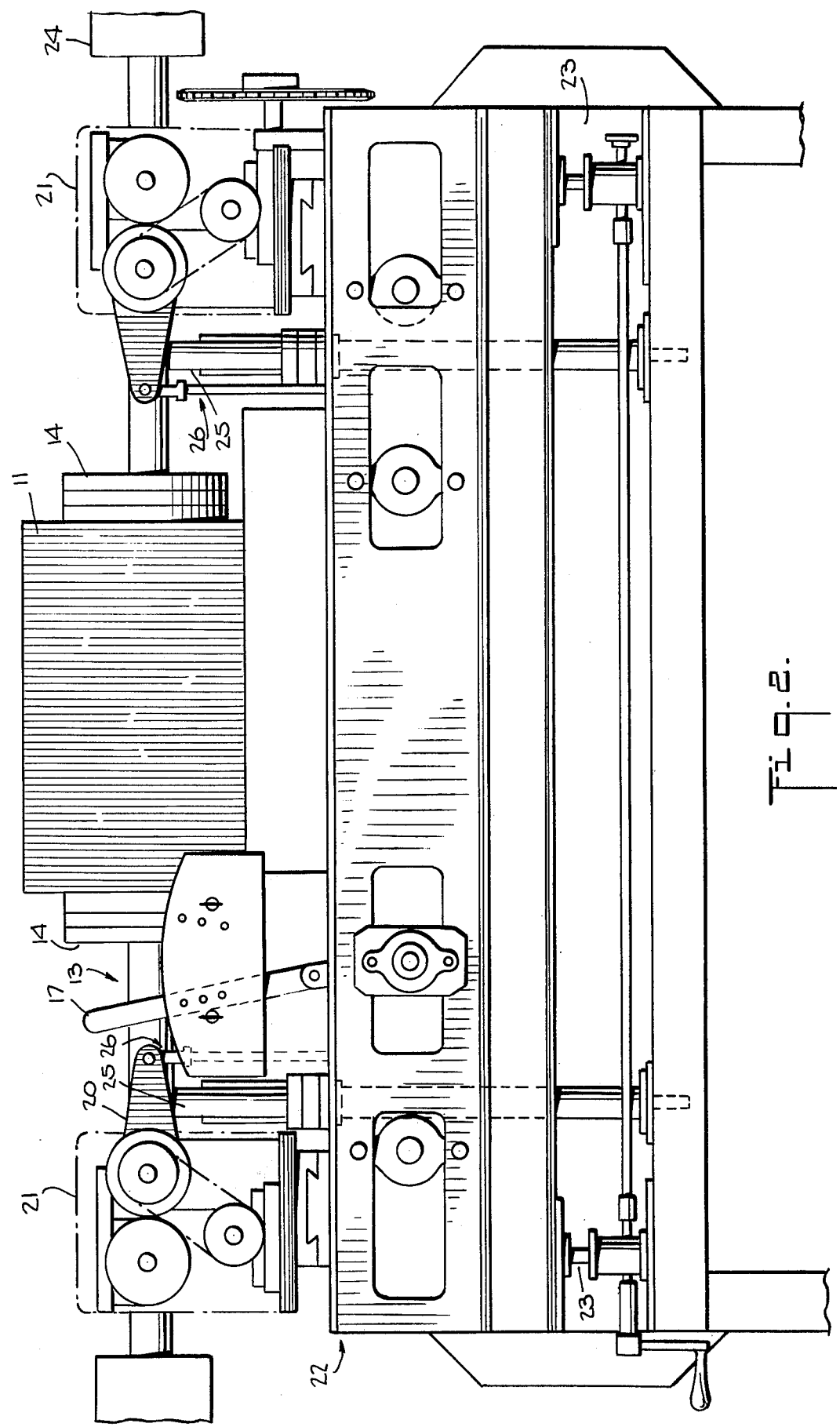

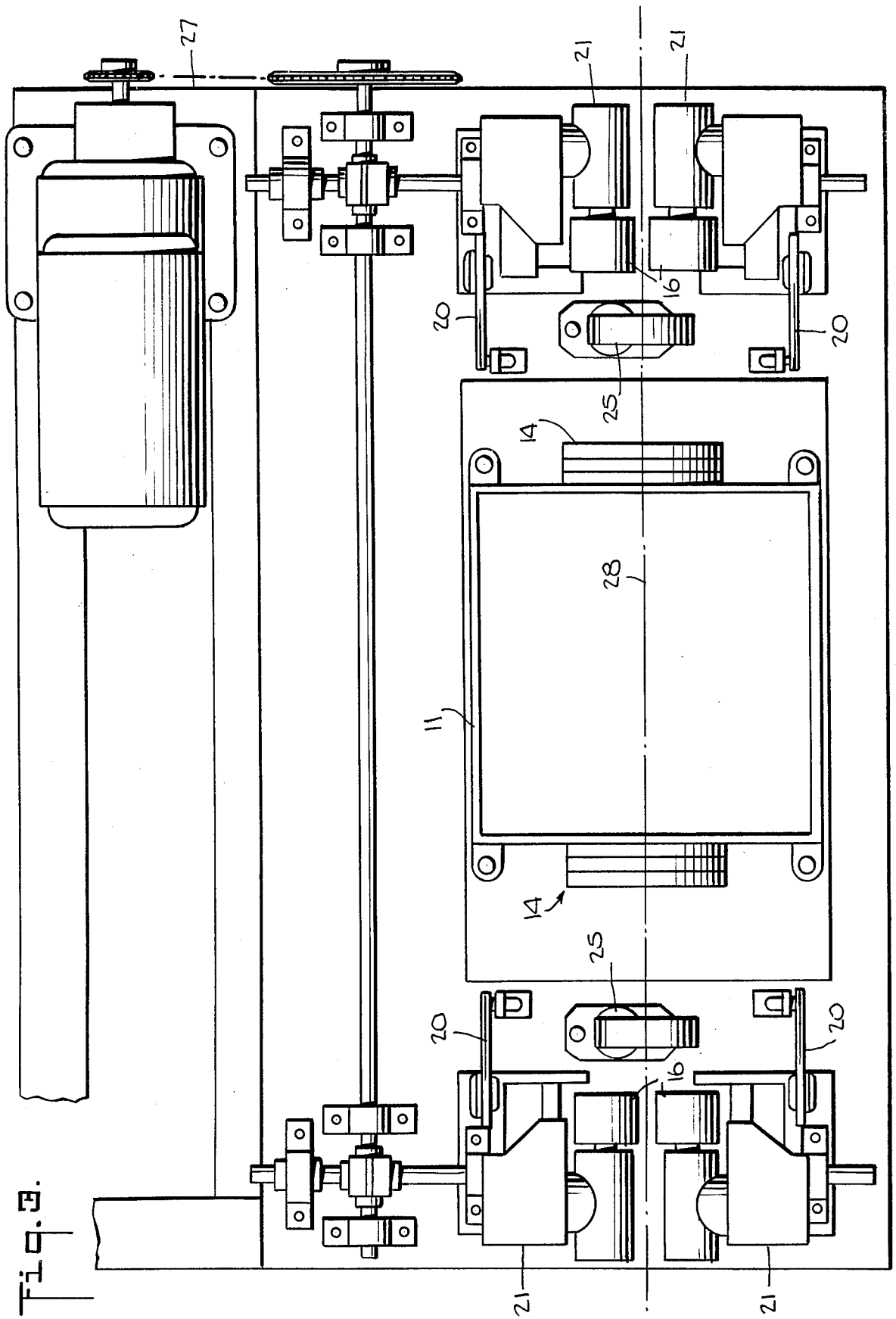

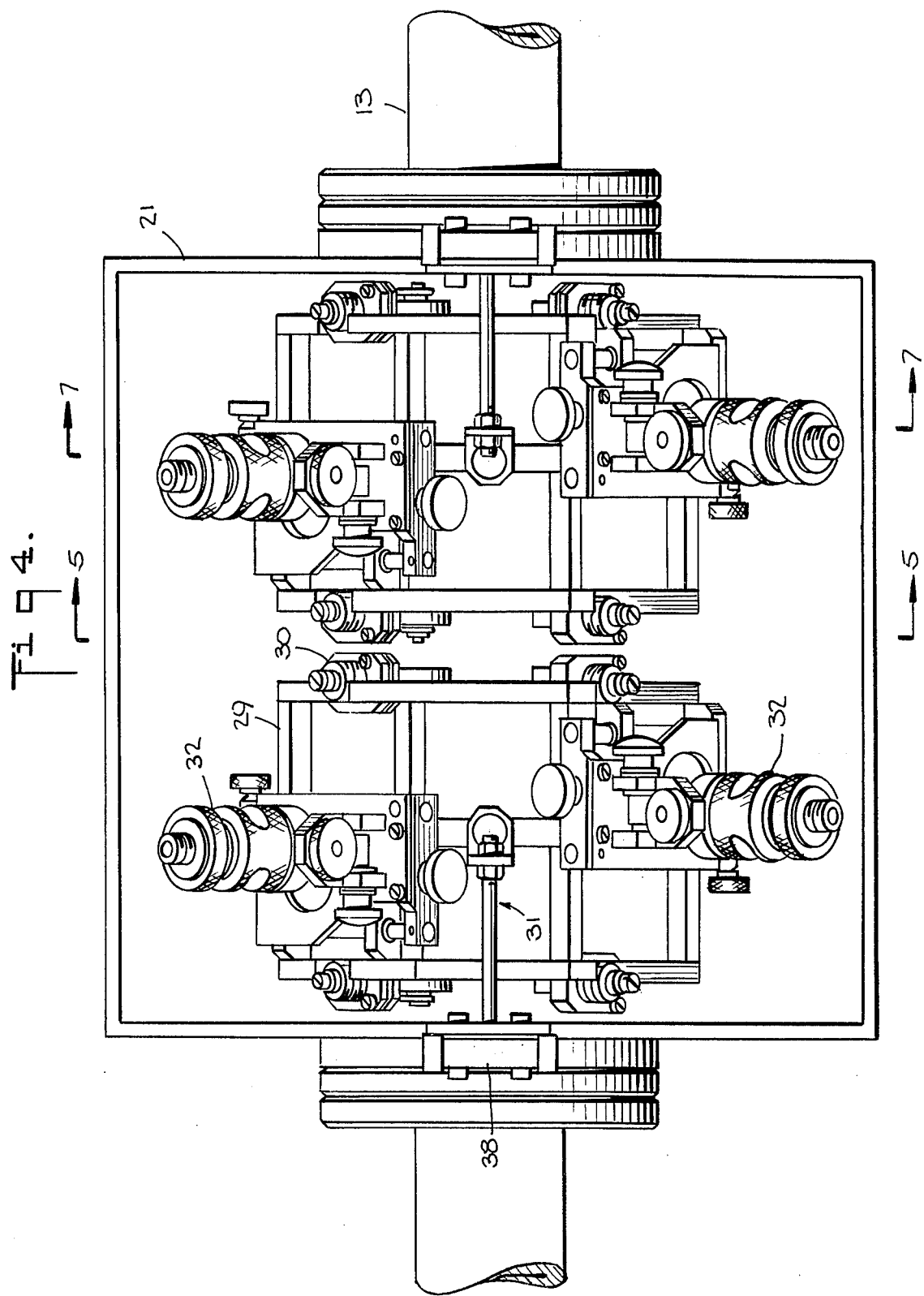

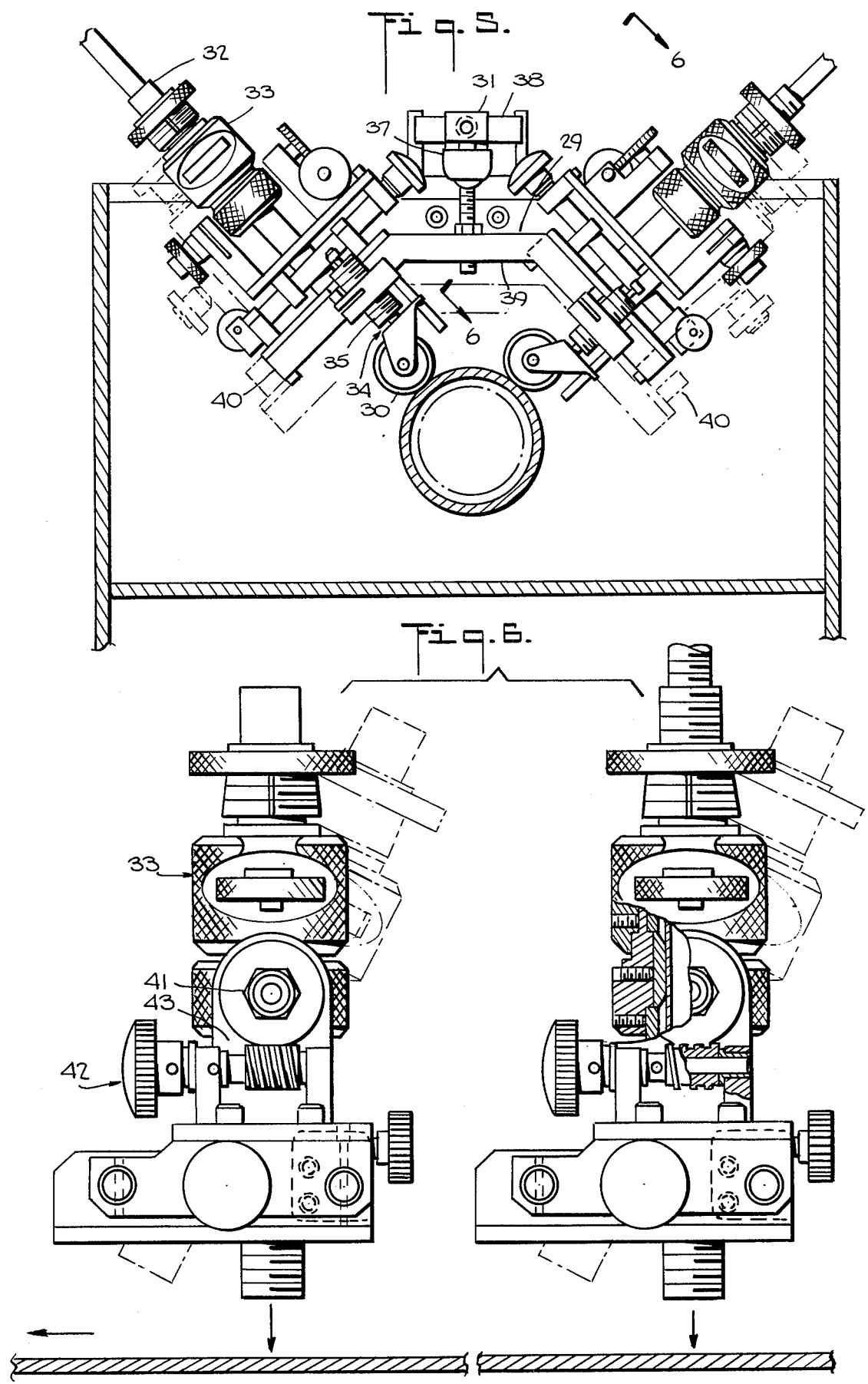

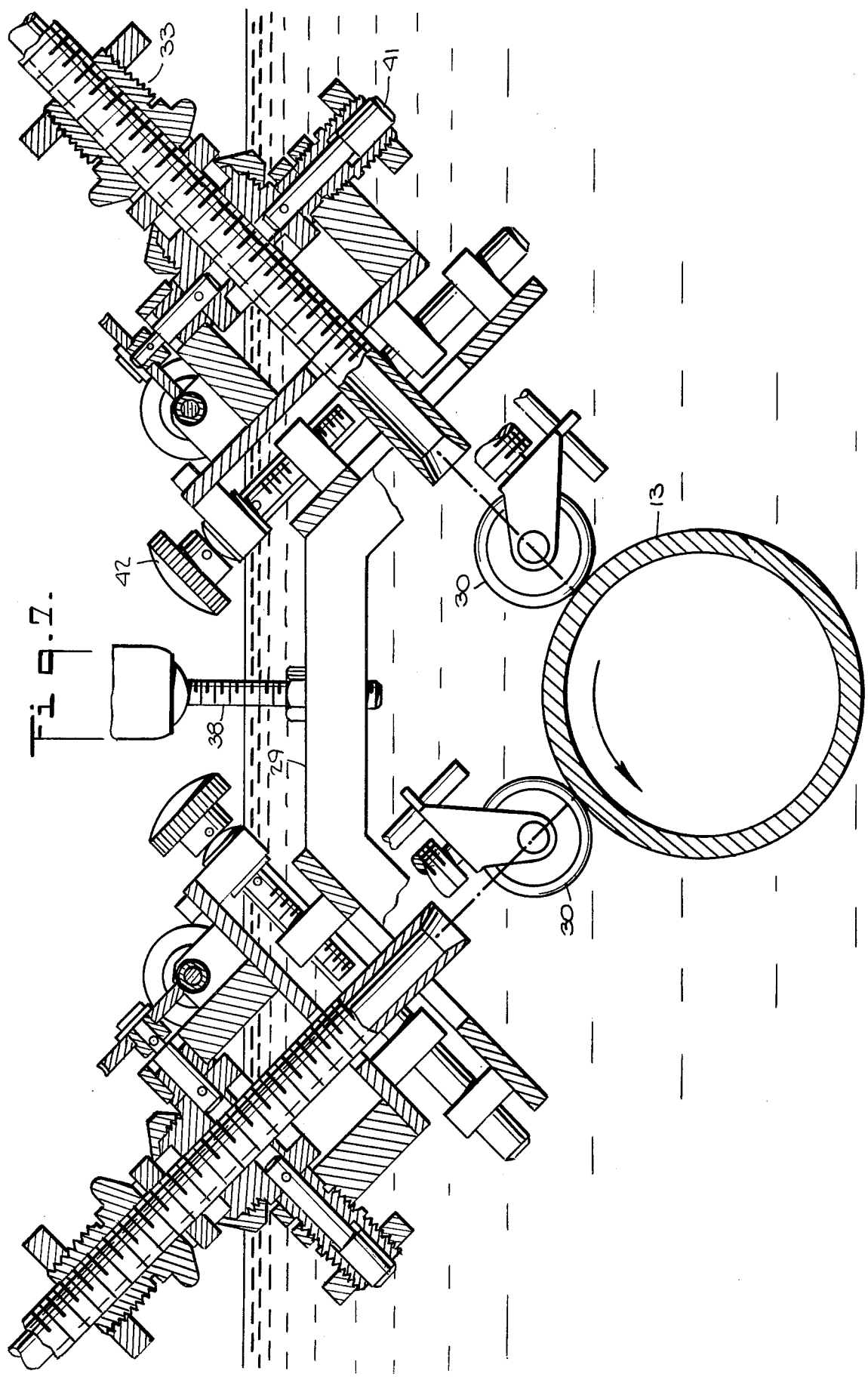

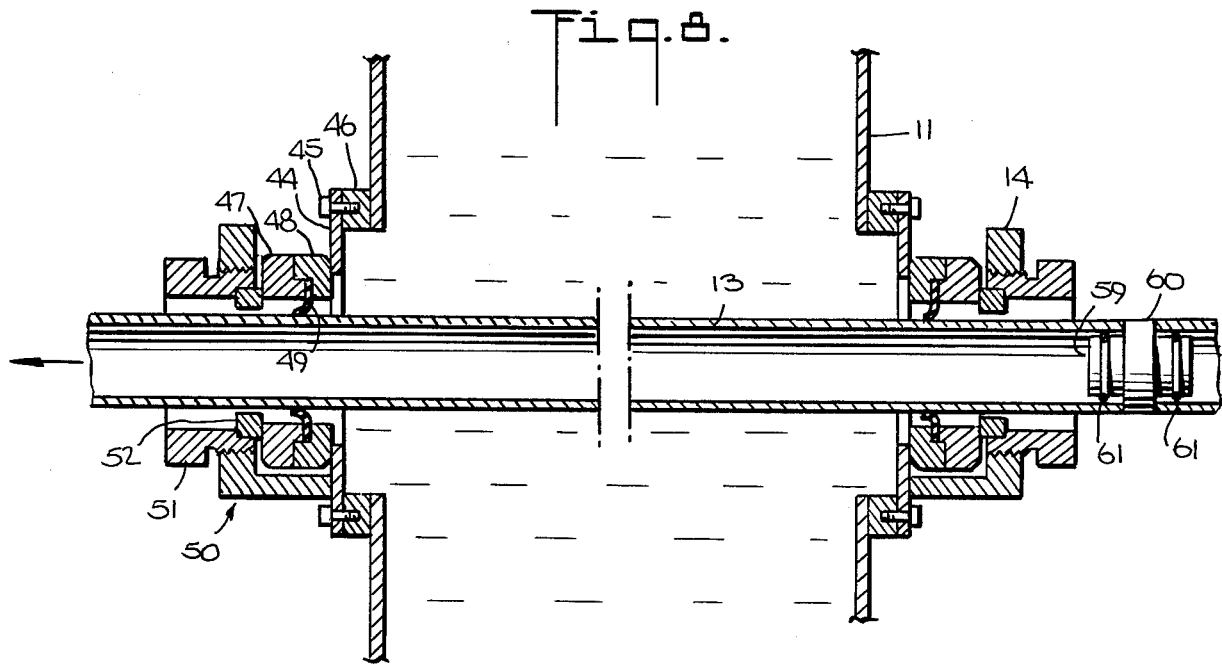
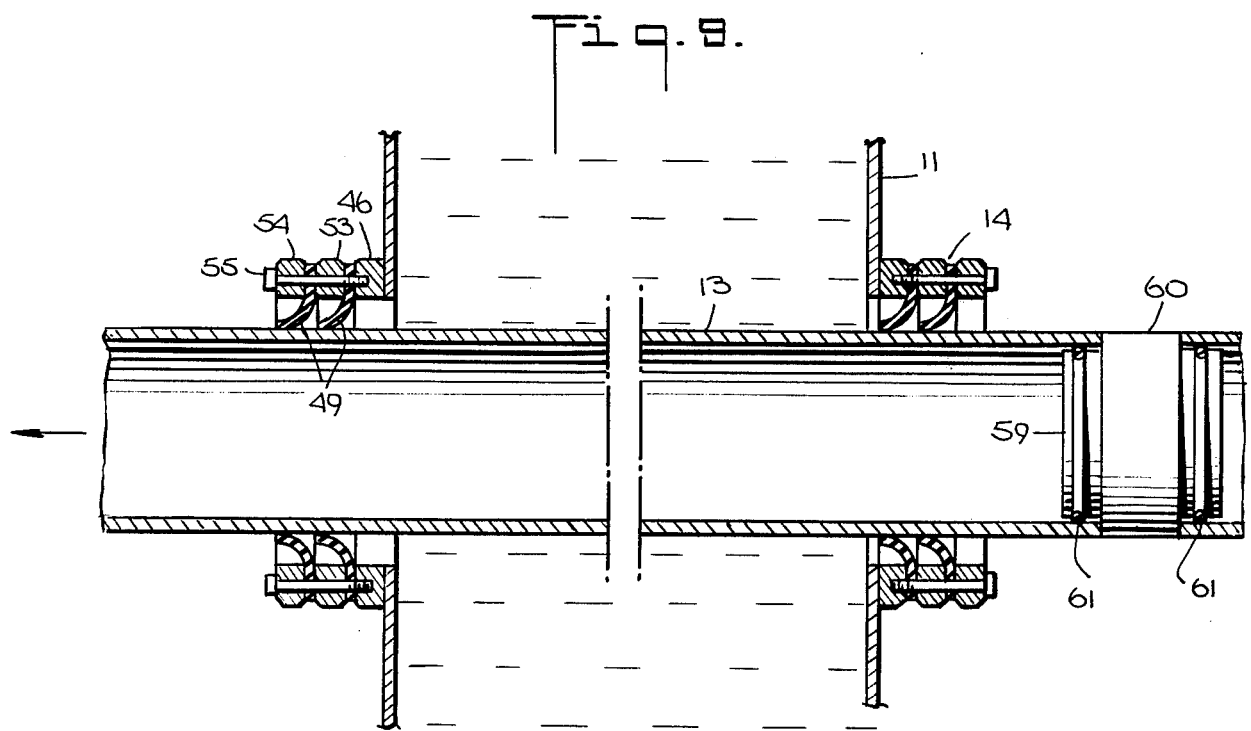

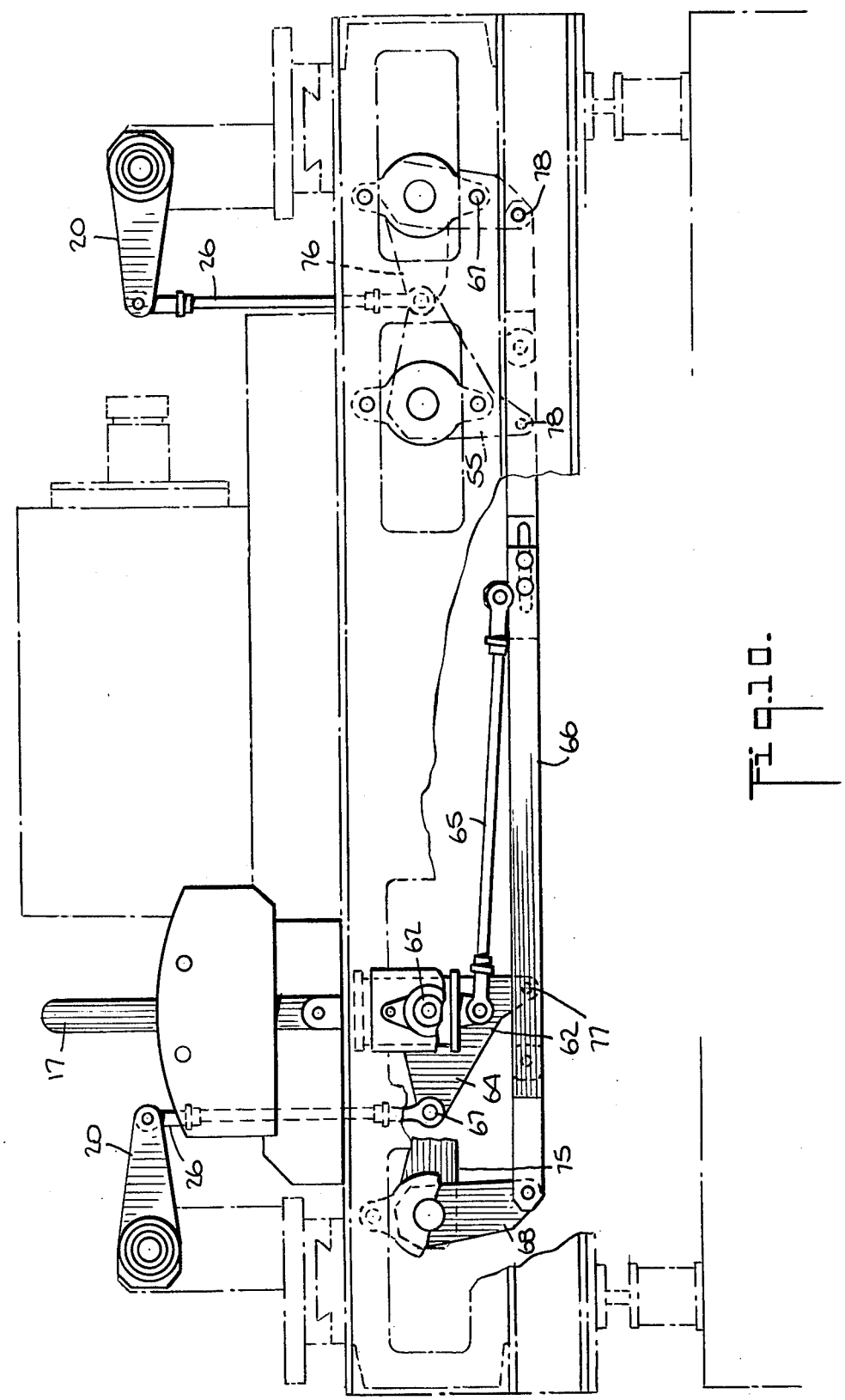

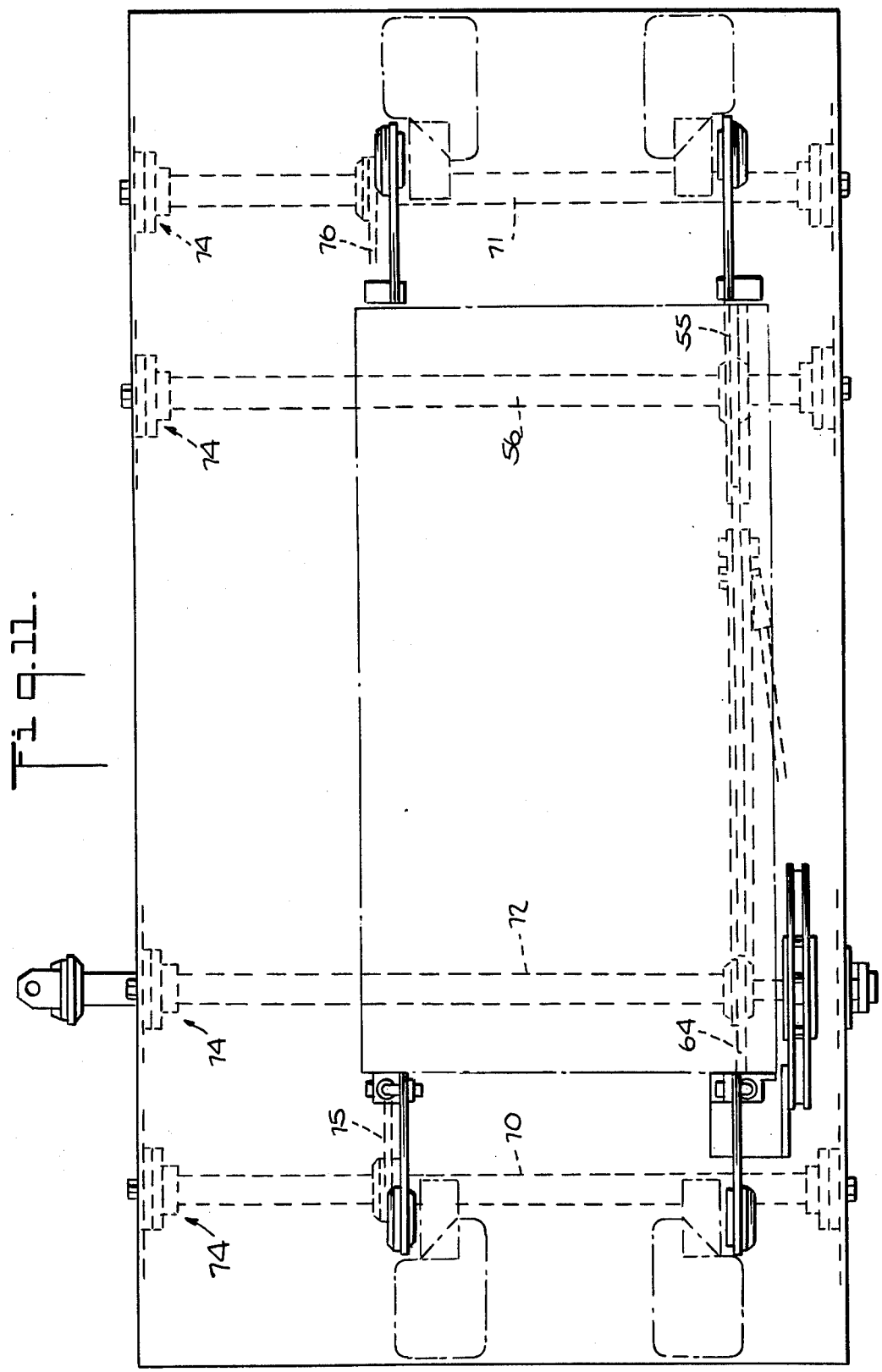

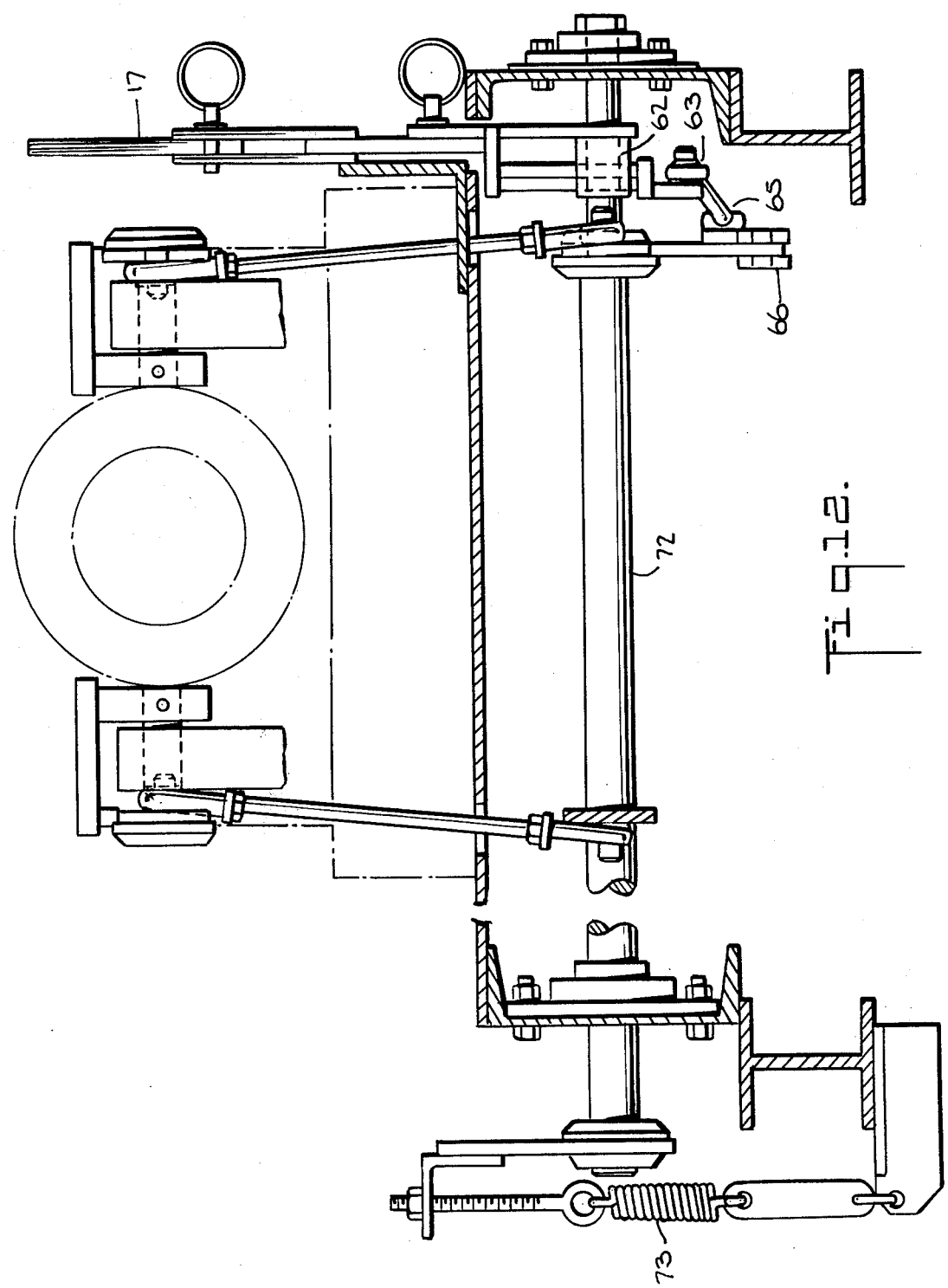

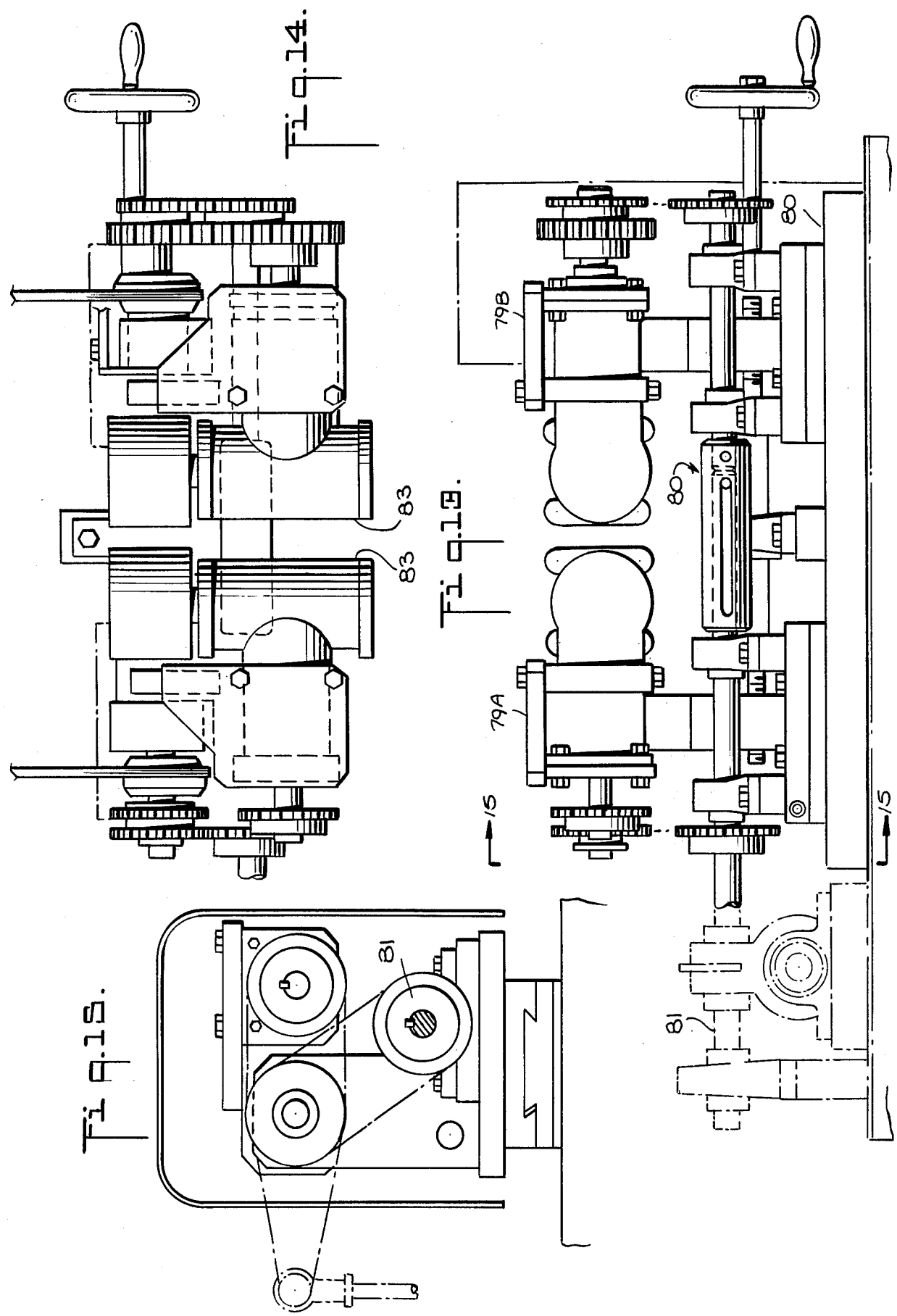

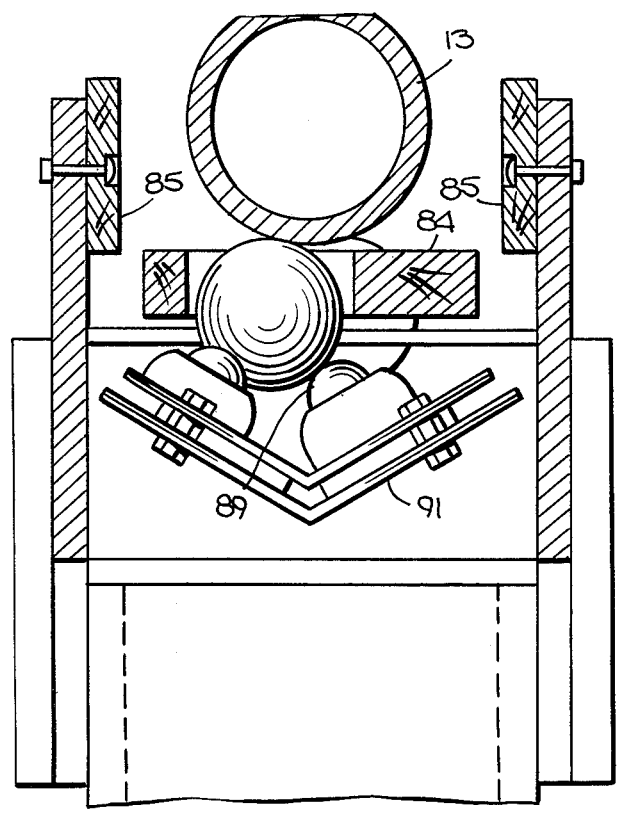
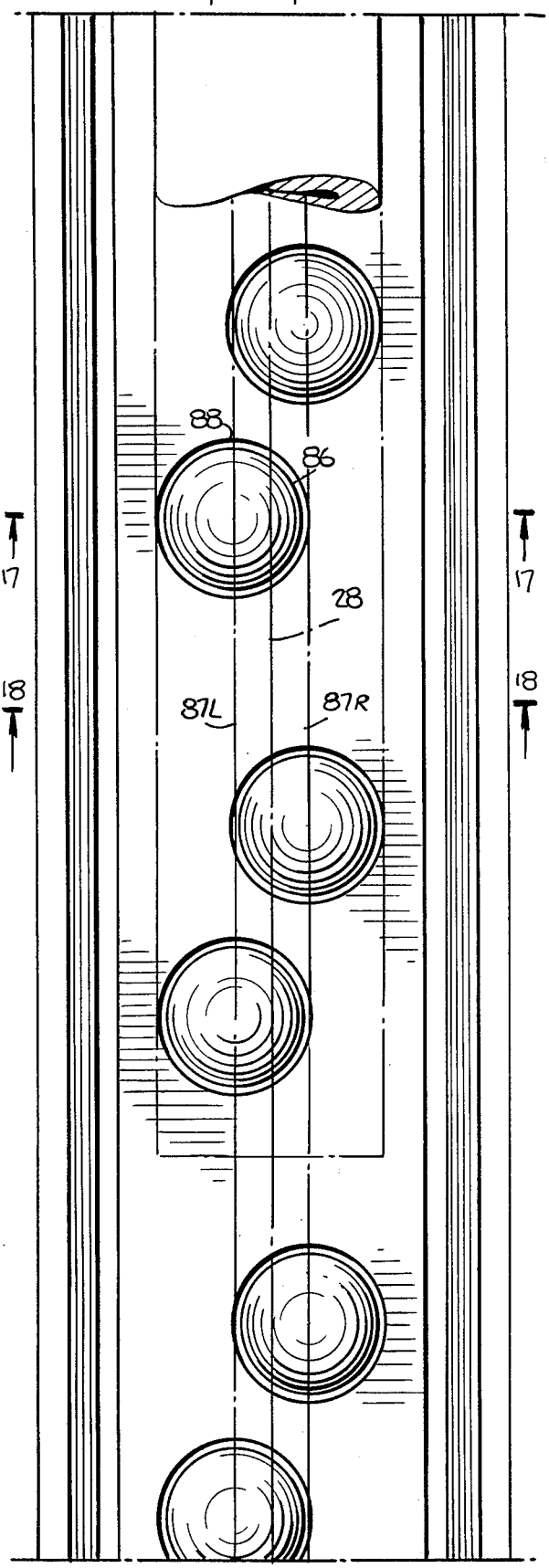
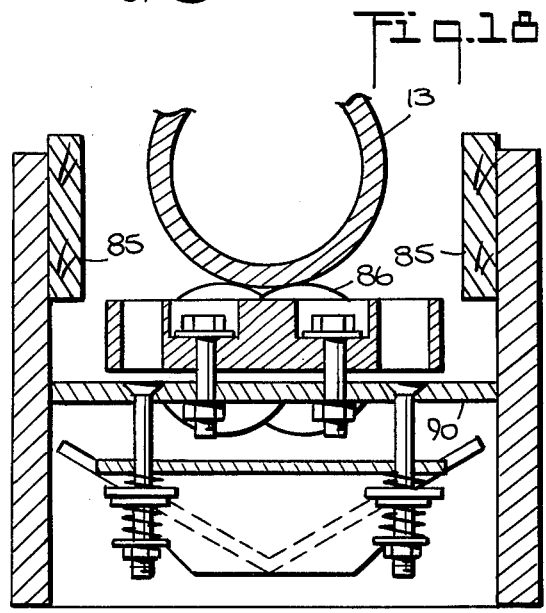

APPARATUS AND METHOD FOR ULTRASONIC INSPECTION OF ROUND STOCK SUCH AS TUBING, PIPE AND ROD

This is a continuation of application Ser. No. 909,769, filed May 26, 1978, now abandoned.

The present invention is directed to an apparatus and method for ultrasonic testing of round stock such as rods, pipe or tubing and more particularly to apparatus and method for expeditiously conducting accurate ultrasonic testing and inspection of such material.

BACKGROUND OF THE INVENTION

Ultrasonic testing is a widely used technique employed to detect defects either on the surface or buried within the interior of round stock such as pipe, tubing or rod. The transducer and electronic equipment employed in conducting ultrasonic testing is commercially available and is reliable. The problems in ultrasonic testing reside in the areas of material handling and prevention of surface damage to the stock being subjected to this popular nondestructive testing technique. In addition, it is recognized that the transducer head or ultrasonic probe must be coupled to the work being inspected through a liquid such as water. Since water immersion of the probe head is required, the probe head must be mounted in a water tank. The work to be inspected must then be transported through the water tank beneath the inspection head. In order that the test be valid, every portion of the material being inspected must be subjected to the transmitted ultrasonic beam. It is recognized that a convenient way of accomplishing this necessary step is to rotate the work being inspected and advance it relatively slowly beneath the test head with the resultant motion of a point on the work being inspected being in the form of a helix with a relatively small angle measured with respect to a circumferential plane passing perpendicularly through the work being inspected. In order to permit the inspector to confirm indications of a defect, it is a requirement that the advance of the work through the water tank be capable of being halted or even reversed so that indications of a defect can be confirmed and the location of the defect marked by the inspector. This means that apparatus is needed for passing the work through the water tank on a continuous basis with the provision that the work be halted in its forward progress or reversed as required. In addition, in the inspection of tubular stock in which many pieces need to be checked during the course of the working shift, means must be provided to prevent water leakage occurring as the end of the tube clears the gland at the end of the water tank since any water which gains access to the interior of the tube will produce false ultrasonic readings. In addition, material handling means such as conveyors, troughs and the like need to be provided at each end of the inspecting device so that a number of objects to be inspected can be handled expeditiously during the course of a shift. It is essential that the inspection head itself be constructed in such a way that the distance between the ultrasonic probe and the surface of the work to be inspected remains essentially constant during the course of the test regardless of whether the work is halted or reversed in its forward progress beneath the inspection head. Various means exist for handling the materials to be tested, which materials will vary in diameter and in length, for transporting the materials through the water tank bearing the ultrasonic testing head and for supporting the ultrasonic testing head in relation to the work being inspected. All of the existing means as far as is known to the present applicants possess certain disadvantages which reduce the productivity of the inspector during the course of a shift. It is of course to be appreciated that the objective of conducting an inspection is to permit the inspector to spend as much time as possible actually performing an inspecting operation and is only required to perform the barest minimum in terms of materials handling of material to be inspected. Furthermore, the requirement of protecting the surface of the work being inspected is highly important since the operation is not successful if it succeeds in generating more scars on the material undergoing tests than it detects in terms of pre-existing defects. Known designs in respect of the transducer support suffer in that they either do not permit linear travel of the product under test, do not permit varying the helical path of the work beneath the test head, or employ means such as ball contacts in supporting the test head which provide disadvantages from the aspect of generating a high risk of product surface damage during the course of the test. Thus, ball cup contact arrangements are known but experience has demonstrated that such arrangements are not tolerant of dirt and grease on the product and are subject to seizure which may cause surface damage to the material being tested. In addition, other undesirable features exist with respect to available transducer supports, for example, counterweight arrangements are sometimes employed which can lead to faulty tests if not maintained in proper adjustment. A requirement for continually checking adjustment of equipment of course interferes with the principal objective of the inspection which is to keep the inspector busy inspecting.

SUMMARY OF THE INVENTION

The invention is directed to the ultrasonic inspection and testing of round stock such as tubing, pipe and rod wherein the ultrasonic testing heads are borne upon a carriage which rides directly upon the work to be inspected as it passes through a water tank and beneath the inspection unit immersed in the water bath to couple the ultrasonic probe to the surface of the work being inspected. In accordance with the invention ordinary lack of straightness or lack of concentricity can be accommodated without interfering with reliability of the ultrasonic test results since the distance between the ultrasonic probe and the work surface being examined is maintained constant.

DRAWINGS

In the accompanying drawings:

FIG. 2 depicts a front elevation of the inspecting machine provided in accordance with the invention;

FIG. 3 represents a plan view of the aforesaid inspecting machine;

FIG. 4 depicts an overall top view of the special ultrasonic testing head contemplated by the invention;

FIG. 5 depicts a cross sectional view taken at section 5—5 of FIG. 4 of the special ultrasonic testing head provided by the invention;

FIG. 6 depicts a cross sectional view taken at section 6—6 of FIG. 5 of the special ultrasonic testing head provided by the invention;

FIG. 7 depicts a cross sectional view taken at section 7—7 of FIG. 4 of the ultrasonic testing head provided by the invention;

FIG. 8 depicts a cross sectional view in elevation on a plane through the longitudinal centerline of a tube being inspected showing the gland design at the ends of the water tank employed for tubes of relatively smaller diameter;

FIG. 9 depicts a cross sectional view in elevation on a plane through the longitudinal centerline of a tube being inspected showing the gland design at the ends of the water tank employed for tubes of relatively larger diameter;

FIG. 10 depicts in partial section the front elevational view of the control linkage for adjusting the skew of the skewed pair drive rolls employed at each end of the water tank for driving round stock therethrough during inspection;

FIG. 11 depicts in partial section the plane view of the aforesaid control linkage;

FIG. 12 depicts in partial section the end elevational view of the aforesaid control linkage at section 12—12 shown in FIG. 11;

FIG. 13 depicts an end elevational view illustrating the mechanical arrangement of a pair of skewable drive rolls for rotating and driving round stock to be inspected through the water tank and beneath the ultrasonic inspection head;

FIG. 14 depicts a plan view of the mechanical arrangement illustrated in FIG. 13;

FIG. 15 depicts an end elevational view of the drive box illustrated in FIGS. 13 and 14;

FIG. 16 depicts a plan view of the special material handling table located outboard at each end of the skewable drive rolls to handle round stock before and after inspection;

FIG. 17 depicts in partial section an elevational view of the aforesaid material handling table with work in place thereon;

FIG. 18 depicts a further cross sectional view in elevation of the aforesaid material handling table; and FIG. 19 illustrates positioning of the larger plastic ball upon which material being processed on the table is supported showing location of the bearing clusters therefor.

Figure 1:
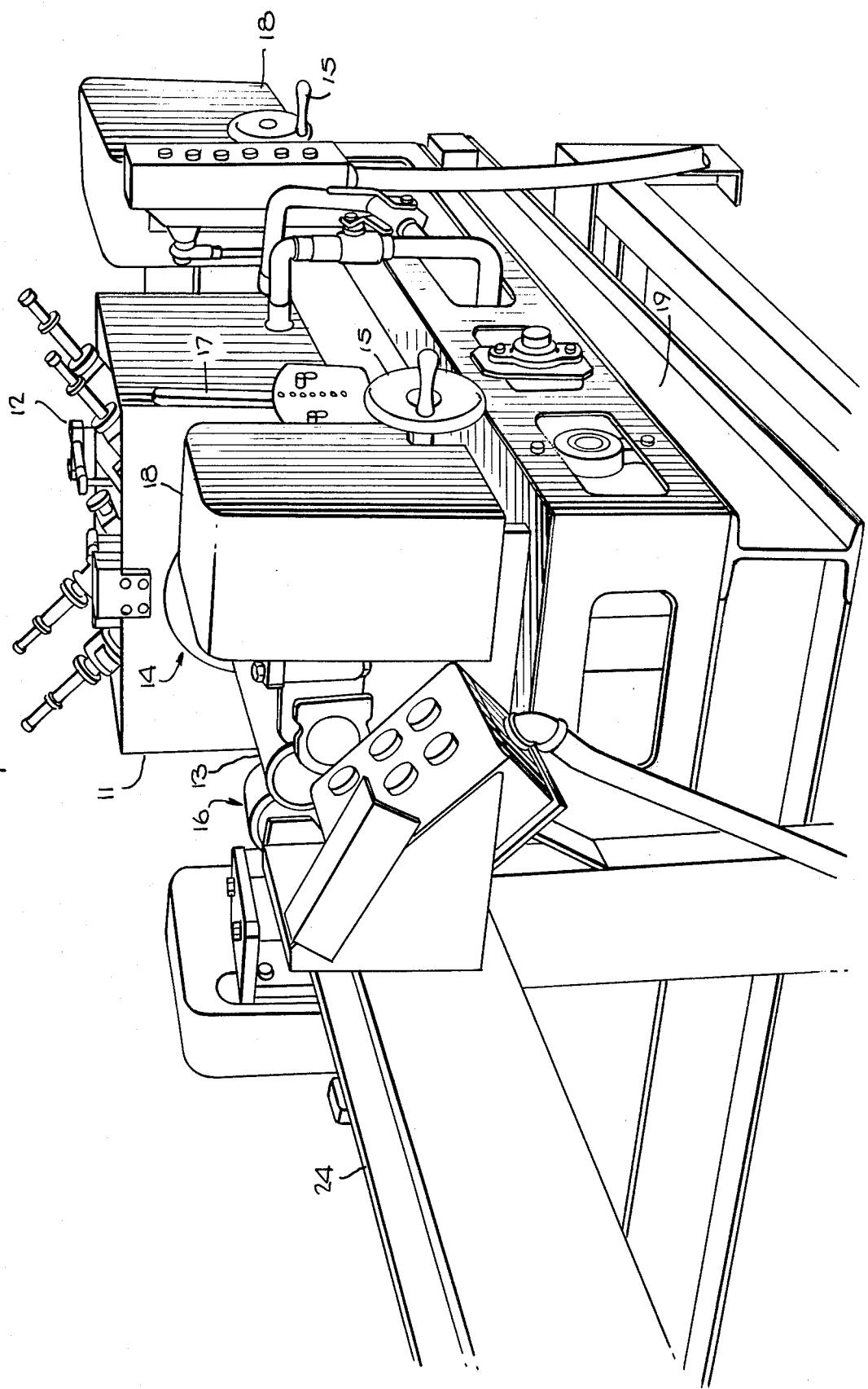
FIG. 1 depicts an overall view of the inspecting machine provided in accordance with the invention.

In general, the invention comprises apparatus and method for ultrasonically inspecting round metal stock, such as rod or tubing quickly, economically and accurately. The apparatus comprises a water tank having glands on opposite sides to permit passage of round stock to be inspected without loss of water from the tank, a carriage to hold the ultrasonic probe or probes employed arranged to ride upon the surface of the round stock to be inspected during passage of the round stock through the water tank, with the carriage weight being supported on the work surface by casters, means for driving the round stock through the water tank rotationally and translationally and work tables at each end of the tank to hold the work prior to and subsequent to ultrasonic inspection. Rotation of the work during inspection must be in the same direction with the resultant of the rotation and translation effects imparted by the drive means presenting the round stock surface in a helical manner, the helix angle being variable from +15° to −15° from the vertical.

The carriage design with casters supporting the carriage weight directly upon the surface of the round stock being inspected provides an essential condition of the invention that the distance between the ultrasonic probe to the surface of the work be maintained constant through the water path despite lack of straightners or concentricity which almost always causes wobbling of the work surface over the supported distance of the work undergoing inspection. The carriage must always provide a rigid platform for mounting the probes accurately and rigidly with respect to the angle to and distance from the work surface.

The distance from the carriage to the caster wheels is adjustable. Adjustments are necessary to provide a geometric relationship whereby a line beginning at the center of the pipe or rod under test and extended through the axle of the caster wheel will be parallel to the centerline of the pivot pin about which the caster swivels. This insures that as the caster turns in relation to the helical travel of the pipe or tube under test that the caster will neither allow the carriage to ride closer nor further away from the surface of the pipe or tube under test. It is necessary that the caster wheel be wide enough to allow that when the angle, created between a line parallel to the centerline of the caster wheel axis and a line parallel to the lengthwise centerline to the pipe or tube under test intersect, is greatest, the contact point on the caster wheel will remain on the surface of the tube closest to the carriage. This relationship requires the pipe or rod feed only in a helical manner through the water box. The direction of rotation must remain constant but the linear travel may be in either direction at any helical angle within the limits of the machine. Various diameters of pipe or rod may be accommodated by adjustment of the caster wheel locations.

The transducer (ultrasonic probe) holder assembly provides for adjustments which accurately positions the transducer such that the location and angle which the sound beam enters the pipe or tube is controlled. Locking arrangements are provided with every adjusting device to insure that transducers will remain in a locked position during the course of testing insuring the accuracy of the test.

Advantageously, the carriage comprises a central table, which may be slotted, having oppositely extending wings angled downwardly at 45° to the central table, thus facilitating location of ultrasonic probes on the wings at an angular displacement of 90°. Desirably, the caster wheel is sufficiently wide that the caster wheel centerline will always intersect the same relative line parallel to the lengthwise centerline of the work being inspected that the caster wheel rides upon when the work helix angle is 0°.

The caster wheel advantageously is non-metallic preferably an elastomeric or polymeric material such as polyurethane, nylon, rubber, etc. A ceramic material could be used. Metallic wheels are less desirable as there could be a tendency for such wheels to slide or skid on the work surface with the resulting possibility of scratching the work surface. Dirt accumulation also becomes more of a possibility. The wheel should rotate even though submerged in water and should be of a long wearing material.

The invention will now be described in more detail in reference to the drawing in which FIG. 1 illustrates an overall view of the testing machine provided in accordance with the invention. In FIG. 1 reference character 11 depicts the water tank in which the ultrasonic testing head depicted generally at 12 is immersed during the course of the test and through which the work 13 illustrated as a tube emerging from the water tank after completion of a portion of the test thereon is shown. Gland 14 at the end of the water tank prevents leakage of water from the tank as the tubular work emerges therefrom. Hand wheels 15 govern the distance between the paired skewable drive rolls which are located at each end of the water tank and are used for the purpose of rotating the work to be inspected and of driving the work in a translational direction depending on the needs of the inspector. Control lever 17 permits the operator to move the work forward, to halt it, or to reverse the translational direction of the work while it continues to rotate in the same direction. In this way, suspected defects may be passed repeatedly beneath the ultrasonic head so that indication of defects can be confirmed. A feature of the skewable drive rolls is that the rolls in the forward position at any one time drive the work forward less rapidly than do the drive rolls at the rear end of the work. This is accomplished by a lever system for adjusting the skew of the paired rolls such that the skew angle of the rearward set of rolls is always greater than the skew angle of the forward set of rolls when the material is being translated through the water tank. It is to be understood that the direction of rotation of the round stock such as a pipe or rod being subjected to tests is always the same, although the speed of rotation is variable depending upon test requirements. The helix angle of the work being tested is instantly adjustable by action of the control lever 17 manipulated by the operator and without stopping the rotation of the material under test. The helix angle is variable from $-15°$ to $+15°$ from $0°$ at which point the pipe or rod does not travel in a linear direction. An integral part of the helix angle change system is the linkage arrangement which automatically provides that the ends of the work pieces, i.e. rod or pipe, being fed in series through the machine will remain in contact regardless of the helix angle or direction of linear travel. These features provide the operator control of the material feed for machine calibration, for application of defect signals, and uninterrupted feed of pipes or rods in a continuous stream end to end. Housings 18 cover the drive mechanisms for the paired skewable rolls. The machine is mounted on a rigid frame indicated generally at 19.

FIG. 2 is a front elevational view of the machine from the operator's vantage point. Visible are the control lever 17, the water tank 11, the glands 14, the work piece 13, the skew control levers 20, the roll drives 21 and the mounting table 22. Vertical adjustment of the table 22 is accomplished by means of jacks 23. Adjustment of the jacks permits vertical height adjustment of the entire testing assembly including the drive rolls and the control assembly at a single time thereby permitting relatively easy adjustment of the test assembly with respect to the material handling tables 24 which are thereby permitted to remain in place. Also visible are the idler wheels 25 which are covered with a resilient material and help provide additional support for the work piece prior to and subsequent to the test. Connecting rods 26 which move the skew control levers 20 are also shown.

In plan view FIG. 3 the water tank 11, glands 14, idler wheels 25, paired skewable drive rolls 16 are shown. The skew control levers 20 are also depicted and the roll drives are also shown. It is made evident that each pair of roll drives are skewed at the same time and to the same extent but in opposite directions so that rotational and linear drive of work through the water tank and under the inspect on head is accomplished. The facings of the drive rolls are of resilient material such as rubber as is the facing of the idler wheels 25. The main motor drive is depicted generally at 27. It will be seen that the pass line for material indicated generally at 28 passes between the skewable drive rolls and through the center of the glands 14.

FIG. 4 is an overall top view depicting two of the special ultrasonic testing head assemblies contemplated in accordance with the invention located within the tank 11 and riding on the surface of the work 13. The test assembly consists of a carriage 29 provided with four casters 30 which ride on the rotating surface of the work 13. A detent 31 which does not support any of the carriage weight is employed to position the carriage so that it does not move laterally and does not roll over on the surface of the work. The ultrasonic probes are indicated generally at 32.

FIG. 5 is a front elevational view of the ultrasonic test head taken at the location 5—5 of FIG. 4. The manner in which the casters ride upon the upper surface of the rotating work is shown. The casters are rotatable about the shaft 34 and are adjustable with respect to carriage 39 by means of the locable screw adjustments 35. The detent arm 36 is fastened rigidly to carriage 29 but is pivoted to the detent by means of the spherical joint depicted at 37. The detent support indicated at 38 and also shown in FIG. 4 is not rigidly attached to the tank but is permitted to ride up and down as needed in response to wobbles caused by lack of straightness of the work. The lockable adjustment of the casters is necessary to provide a geometric relationship whereby a line beginning at the center of the round stock under test and extended through the axle of the caster wheel will be parallel to the center line of the shaft 34 about which the caster swivels. Conveniently the carriage 29 takes the form as shown wherein a center table 39 is provided having downwardly extending wings 40 at an angle of 45° to the table thereby permitting ready mounting of the probe holders 33 rigidly to the wings 40 in such a manner that the included angle between the probe holders and the probes therein is 90°. As shown in the figures, the casters are displaced laterally on the carriage from the probe holder 33 so that the necessary coupling of the transducer to the work surface through the water in water tank 11 is accomplished.

FIG. 6 is a view taken at section 6—6 of FIG. 5 showing that the probe holder 33 may be rotated about the pivot 41 as desired. Adjusting wheel 42 having a screw threaded shaft 43 is employed for this purpose.

FIG. 7 is a cross sectional view of the testing head 12 through section 7—7 of FIG. 4. The probe holder 33 is depicted as an internally threaded tube in which the probe instrument itself may be located at the desired distance from the work and locked firmly in place.

FIGS. 8 and 9 illustrate gland designs for sealing about the round stock as it progresses through the water tank 11. FIG. 8 illustrates a gland design employed for a smaller size stock such as sizes up to approximately 3 inches in diameter, whereas FIG. 9 illustrates a gland design employed for larger size tubing above about 2½ or 3 inches in diameter. In FIG. 8 the gland comprises an orifice plate 44 fastened firmly as by cap screws 45 to a mounting ring 46 which is mounted to the tank 11. Nylon rings 47 and 48 cooperate to hold rubber diaphragm 49 in water-tight relation. The mounting body 50 is fastened to orifice plate 44 and is internally threaded to receive locking ring 51 which seats against tube guide 52 and holds it securely in place. Tube guide 52 may also be made of an elastomeric material such as nylon. The simpler structure used on the larger size tubing illustrated in FIG. 9 also comprises a mounting ring 46 with two nylon rings which are bolted to ring 46 by means of bolts 55 so as to hold securely the rubber diaphragms 49 therebetween.

A further feature set forth in FIGS. 8 and 9 is the method for sealing the joint between adjacent tubes being fed through the testing head. As noted previously, the drive system provided in accordance with the invention furnishes a positive force on the tube by adjusting the drive rolls such that the rearward set of rolls pushes the tube forward harder than the forward motion imparted to the work by the forward set of drive rolls. Accordingly, as a tube end approaches the water tank, a plug 59, having a centrally-located circumferential boss 60, which can be made of metal is inserted in the end thereof and the next tube to be examined of the same size is placed over the trailing end of the plug. O rings 61 may be provided circumferentially around the plugs. The positive force applied by the drive system maintains the ends of the two tubes in close contact under positive pressure as the joint is passed through the water tank under the inspection head. In this way, leakage of water to the tube interior, an event which would cause false readings from the ultrasonic testing system, is prevented.

FIGS. 10, 11 and 12 depict the drive roll control mechanism which insures that a positive force is always placed on the tube or rod undergoing test regardless of the lateral direction in which the work is being pushed. This feature is accomplished by providing automatic control of the skew angle of the rearward set of drive rolls such that it is always slightly greater than the skew angle of the forward set of drive rolls. In this way, while the forward set of rolls is still rotating and driving the tube forward, the rate at which it is driving the tube forward is slower than the rate at which the rearward set of rolls is driving the tube forward. As shown in the figures control lever 17 which is employed by the operator to control the lateral speed and direction of the tube undergoing test is supported by bushing 62 on shaft 72 is connected through connecting rod 65 to draw bar 66 at pivot 63. Rocker arm 64 is connected at pivot 67 to connecting rod 26. Draw bar 66 also connects by pivots to rocker arm 55 and levers 68 and 69. Levers 68 and 69 in turn rotate shafts 70 and 71. Rocker arm 64 also rotates shaft 72 which is connected at the other end to an eccentric spring load mount 73. The shafts are provided with appropriate journals 74. Shafts 70 and 71 connect with rocker arms 75 and 76 which drive connecting rod 26 to activate the levers 20. In this way, a single motion of the control lever 17 adjusts the skew levers 20 of both the front drive roll pairs and the rear drive roll pairs. Pivots 77 and 78 which connect draw bar 66 to rocker arms 64 and 67 respectively are located at a small angle from the vertical from the centers of shafts 72 and 74 whereby the skew angle of the rearward driving rolls regardless of the lateral direction of the rod or tube being inspected will always be slightly greater than the skew angle of the forward pair of driving rolls.

FIG. 13 is an elevational view of the skew pair drive roll driving and adjusting mechanism. Each drive roll assembly indicated generally at 79a and 79b is mounted on machine slide 80. The lateral distance between the drive roll pairs is maintained with respect to the work piece pass line by means of mechanism indicated generally at 81 controlled by hand wheel 15. Driving power is communicated to the drive rolls through shaft 81.

FIG. 14 is the plan view of the drive roll assembly as described in FIG. 13. It is to be noted that the drive rolls 16 are driven by pivoted gear heads 83 and that the drive rolls face the water tank at each end.

FIG. 15 is taken at section 15—15 of FIG. 13 and shows the drive arrangement for the skewable rolls.

FIGS. 16, 17, 18 and 19 illustrate the material handling table 24. The table consists of a wooden bottom 84 and wooden sides 85 to form a trough. In the bottom of the trough are mounted two rows of plastic balls 86 with the center lines of each row being spaced to the left and to the right on center lines 87L and 87R which are disposed equidistantly on each side of the material pass center line 28. Holes 88 freely accommodate the balls 86 and the balls 86 are mounted on a cluster of three ball-transfer bearing assemblies 89. Balls 86 clear the holes 88 and since they are mounted on the clustered ball-transfer bearing assemblies, each ball is free to rotate in any direction. As shown particularly in FIGS. 17 and 18 round stock rests on the balls 86 and may either rotate or be moved laterally without risk of damage to the stock 13. The trough bottom 84 is mounted firmly to frame 90. Conveniently the top of the ball projects above the wooden trough bottom by approximately ¼ inch. The ball clusters themselves are rigidly mounted as indicated generally at 91.

Although the present invention has been described in conjunction with preferred embodiments, it is to be understood that modifications and variations may be resorted to without departing from the spirit and scope of the invention, as those skilled in the art will readily understand. Such modifications and variations are considered to be within the purview and scope of the invention and appended claims.

We claim:

1. Apparatus for conducting liquid-submerged ultrasonic testing of round stock wherein the round stock to be inspected is rotated in a single direction and is advanced lengthwise under the ultrasonic head such that a point on the surface of the round stock describes a helical path comprising an ultrasonic test head having a carriage adapted to hold at least one ultrasonic probe in fixed relation thereto, said carriage being mounted on a plurality of casters provided with non-metallic wheels, said casters being arranged to ride on the outer surface of the round stock being inspected and being rotatable about the caster vertical axis such that the rotational axis of the caster wheel is always perpendicular to the pitch of a helix described by a point on the surface of said round stock when said pitch is changed during the course of the test, said casters bearing the weight of said carriage upon the surface of the round stock such that the distance between said ultrasonic probe and said round stock surface is maintained constant during the course of the test, means to vary and reverse the pitch of said helix, adjusting means to adjust the distance from said carriage to said caster wheels such that a geometric relationship is established in which a line extending from the center of the round stock to be inspected through the axle of said caster wheel is parallel to the center line of the pivot pin about which the caster swivels.

2. Apparatus according to claim 1 wherein said caster wheels are made of a plastic.

3. Apparatus according to claim 2 wherein said carriage is located within a water tank having glands at each end to form water seals circumferentially about said round stock to be inspected, combined with means for rotating and advancing said round stock through said tank and horizontal trough means for handling said round stock prior to and subsequent to inspection aligned with the center line through said water tank, said trough means comprising two rows of polymeric balls each mounted upon a cluster of ball transfer bearing assemblies, with each of said rows being located equidistantly from the vertical center line location along which round stock to be inspected is to be passed.

4. Apparatus according to claim 2 wherein said caster wheels are sufficiently wide that the caster wheel center line will always intersect the same line parallel to the lengthwise center line of the round stock being inspected regardless of the pitch or direction of the helix so that the contact point of the caster wheel will remain on the surface of the round stock closest to the carriage.

5. Apparatus according to claim 2 wherein said carriage comprises a central table having oppositely extending wings appended thereto at a 45° downward angle with means upon said wings for mounting ultrasonic probes at a 90° angular displacement therebetween.

6. Method for ultrasonically inspecting round stock comprising passing round stock to be inspected past at least one ultrasonic test head in water-submerged relation with said round stock, while rotating said round stock in the same direction during test and maintaining a constant distance between said ultrasonic test head and the outer surface of said round stock by mounting said ultrasonic test head on a carriage having casters which bear the weight of said carriage and ride upon the outer surface of said round stock, with the distance from the caster wheels to said carriage being adjustable so that a line from the center of said round stock through the axle of said caster is maintained parallel to the center line of the pivot about which the caster swivels to insure that the distance between round stock and carriage does not change during change in pitch or direction of the inspection helix or with change in diameter of said round stock.

* * * * *